United States Patent
Noonan et al.

(10) Patent No.: US 10,463,343 B2
(45) Date of Patent: Nov. 5, 2019

(54) ROBOTIC ACTUATOR FOR TRANSEOPAGEL ECHOCARDIOGRAPHY PROBE

(71) Applicant: KONINKLIJKE PHILIPS N.V., Eindhoven (NL)

(72) Inventors: David Paul Noonan, New York, NY (US); Aleksandra Popovic, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 516 days.

(21) Appl. No.: 15/112,702

(22) PCT Filed: Jan. 16, 2015

(86) PCT No.: PCT/IB2015/050332
§ 371 (c)(1),
(2) Date: Jul. 20, 2016

(87) PCT Pub. No.: WO2015/110943
PCT Pub. Date: Jul. 30, 2015

(65) Prior Publication Data
US 2016/0338667 A1    Nov. 24, 2016

Related U.S. Application Data

(60) Provisional application No. 61/930,983, filed on Jan. 24, 2014.

(51) Int. Cl.
*A61B 34/00* (2016.01)
*A61B 8/00* (2006.01)
(Continued)

(52) U.S. Cl.
CPC .............. *A61B 8/44* (2013.01); *A61B 1/0016* (2013.01); *A61B 8/0883* (2013.01); *A61B 8/12* (2013.01);
(Continued)

(58) Field of Classification Search
CPC combination set(s) only.
See application file for complete search history.

(56) References Cited

U.S. PATENT DOCUMENTS

| | | |
|---|---|---|
| 5,181,514 A | 1/1993 | Solomon |
| 5,320,104 A | 6/1994 | Fearnside |
| 5,771,896 A | 6/1998 | Sliwa |
| 5,906,578 A | 5/1999 | Rajan |
| 5,957,850 A | 9/1999 | Marian |
| 7,547,152 B2 | 6/2009 | Sapir-Haim |

(Continued)

FOREIGN PATENT DOCUMENTS

| | | |
|---|---|---|
| DE | 202010009234 U1 | 12/2011 |
| JP | 3103262 A | 4/1991 |

(Continued)

*Primary Examiner* — Omkar A Deodhar

(57) ABSTRACT

A robotic actuator (30) for controlling one or actuation dials of an interventional tool handle (41) (e.g., a handle of a probe). The robotic actuator (30) employs a coupling of a handle base (34) and a handle cover (33) to define a actuation chamber for housing the actuation dial(s) of the interventional tool handle (41), and one or more motorized gear(s) (31, 32) within the actuation chamber operable to engage the actuation dial(s) of the interventional tool handle (41) within the actuation chamber. In operation, a robotic workstation (20) generates motor commands for controlling the actuation dial(s) of the interventional tool handle (41), and the motorized gear(s) (31, 32) are operably connected to the robotic workstation (20) to control the actuation dial(s) of the interventional tool handle (41) responsive to the motor commands generated by the robotic workstation (20). The robotic actuator (30) may further employ an actuator platform (38) for controlling lateral and/or rotational motion of the interventional tool handle (41).

15 Claims, 6 Drawing Sheets

(51) Int. Cl.
- *A61B 1/00* (2006.01)
- *A61B 8/08* (2006.01)
- *A61B 8/12* (2006.01)
- *A61B 34/30* (2016.01)
- *A61B 90/00* (2016.01)
- *A61B 1/005* (2006.01)

(52) U.S. Cl.
CPC .............. *A61B 8/445* (2013.01); *A61B 8/467* (2013.01); *A61B 8/54* (2013.01); *A61B 34/30* (2016.02); *A61B 90/37* (2016.02); *A61B 1/0052* (2013.01); *A61B 2034/301* (2016.02); *A61B 2090/3784* (2016.02)

(56) References Cited

U.S. PATENT DOCUMENTS

| | | |
|---|---|---|
| 2004/0073083 A1 | 4/2004 | Ikeda |
| 2009/0287043 A1 | 11/2009 | Naito |
| 2010/0268031 A1 | 10/2010 | Koyama |
| 2010/0318100 A1 | 12/2010 | Okamoto |
| 2012/0065470 A1 | 3/2012 | Olds |
| 2012/0089029 A1 | 4/2012 | Harhen |
| 2014/0296633 A1* | 10/2014 | Gumbs ................ A61B 1/0052 600/109 |

FOREIGN PATENT DOCUMENTS

| | | |
|---|---|---|
| JP | 5300873 A | 11/1993 |
| JP | 2013158571 | 8/2013 |
| JP | 2013158612 | 8/2013 |

* cited by examiner

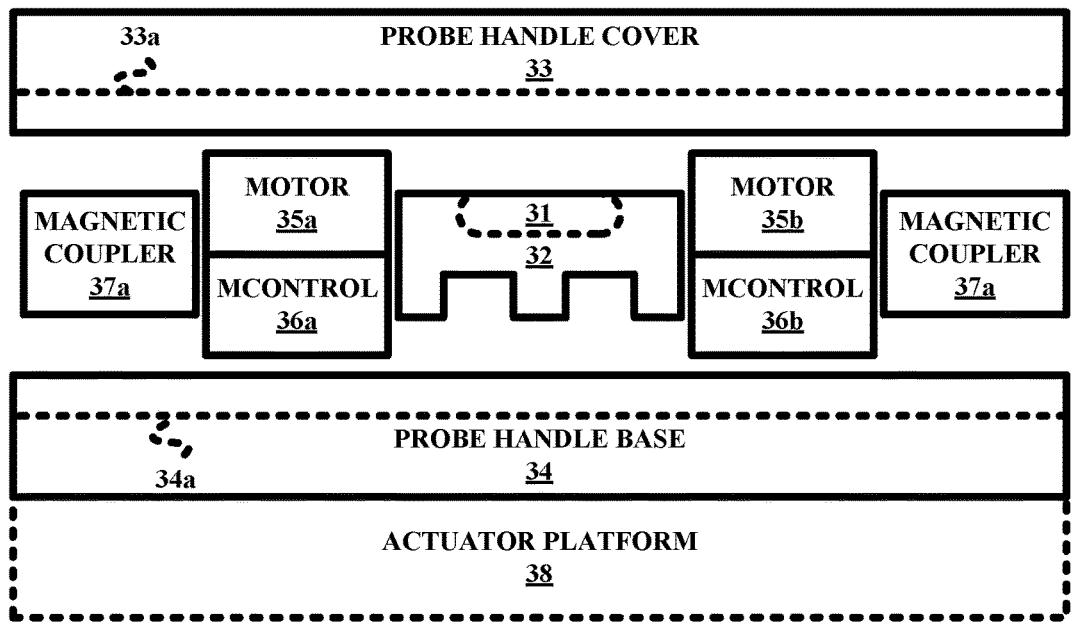
FIG. 5
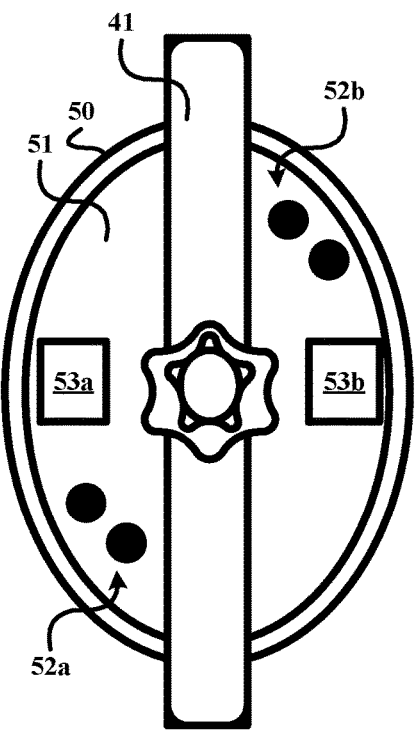 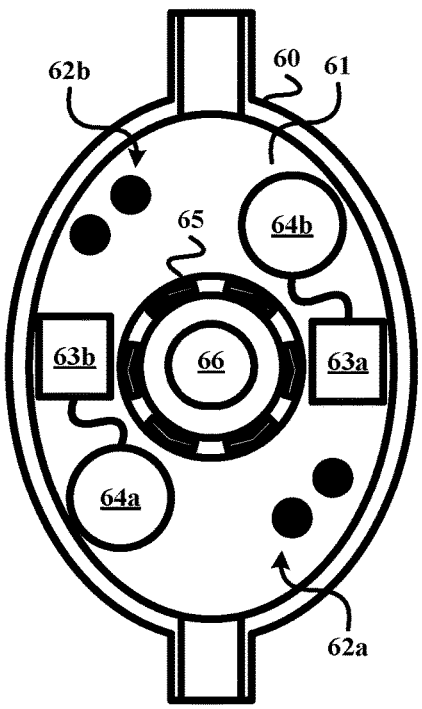
FIG. 6A  FIG. 6B

ROBOTIC ACTUATOR FOR TRANSEOPAGEL ECHOCARDIOGRAPHY PROBE

CROSS-REFERENCE TO PRIOR APPLICATIONS

This application is the U.S. National Phase application under 35 U.S.C. § 371 of International Application No. PCT/IB2015/050332, filed on Jan. 16, 2015, which claims the benefit of U.S. Provisional Patent Application No. 61/930,983, filed on Jan. 24, 2014. These applications are hereby incorporated by reference herein.

The present invention generally relates to transeesophageal echocardiography ("TEE") probes. The present invention specifically relates to a robotic actuation of the TEE probe during an interventional procedure.

Transeesophageal echocardiography is commonly used to visualize cardiac anatomy and interventional devices during treatment for structural heart disease ("SHD"). FIG. 1 shows a typical distribution of theatre staff within a lab room 10a having an ultrasound workstation 11 and an x-ray scanner, of which a c-arm 12 is shown. During a SHD operation, an echocardiographer 13 holds a TEE probe 14, which passes through a mouth of a patient 16 into a esophagus to visualize a heart of patient 16. A cardiologist 15 is located on an opposite side of x-ray c-arm 12 and an operating table 17. Cardiologist 15 navigates interventional devices (not shown) (e.g., catheters and guidewires) from arterial incisions into the heart under x-ray guidance and ultrasound guidance via TEE probe 14 in order to perform different diagnostic or therapeutic procedures. Exemplar procedures, such as mitral clip deployments or transcatheter aortic valve replacements ("TAVR"), can be time consuming and complex. Moreover, ensuring appropriate visualization of the target anatomy during the procedure is the responsibility of echocardiographer 13, who must make constant small adjustments to a position of a tip of TEE probe 14 for the duration of the procedure.

In practice, the operating conditions of FIG. 1 present several challenges. The first challenge is fatigue and poor visualization. Specifically, appropriate visualization includes both ensuring the relevant anatomical structures are within the field of view, and that the necessary contact force between the transducer head and esophageal wall, to achieve adequate acoustic coupling, is achieved. To this end, a position and an orientation of a head of TEE probe 14 requires constant, minute adjustments for the duration of the procedure in order to maintain appropriate visualization of the target structures. This can lead to fatigue and poor visualization by echocardiographer 13 during long procedures.

The second challenge is x-ray exposure. Specifically, a length of TEE probe 14 results in the positioning of echocardiographer 13 in close proximity to the source of interventional x-ray system, thus maximizing the x-ray exposure of echocardiographer 13 over the course of the procedure.

The third challenge is communication and visualization. During certain phases of a procedure, cardiologist 15 and echocardiographer 13 must be in constant communication as cardiologist 15 instructs echocardiographer 13 as to which structure to visualize. Given the difficulty interpreting a 3D ultrasound volume, and the different co-ordinate systems displayed by the x-ray and ultrasound systems, it can be challenging for echocardiographer 13 to understand the intentions of cardiologist 15.

The present invention provides a robotic actuation system to address these challenges. Generally, as shown in FIG. 2, a new distribution of theatre staff within a lab room 10b with the robotic actuator system employing a robotic workstation 20 and robotic actuator 30 for remote control of between two (2) degrees of freedom and (4) degrees of freedom of TEE probe 14 which adjust the ultrasound imaging volume of TEE probe 14. Additionally, as will be further described herein, robotic actuator 30 may have the ability to be retrofitted to existing and various types of TEE probe 14 and may have the ability to be rapidly remove from TEE probe 14 should echocardiographer 13 decide to return to manual operation of TEE probe 14 for any reason.

One form of the present invention is a robotic actuator for controlling one or actuation dials of an interventional tool handle (e.g., a handle of a probe). The robotic actuator includes a coupling of a handle base and a handle cover to define a actuation chamber for housing the actuation dial(s) of the interventional tool handle and one or more motorized gears within the actuation chamber operable to engage the actuation dial(s) of the interventional tool handle within the actuation chamber.

The robotic actuator may further employ an actuator platform for controlling lateral and/or rotational motion of the interventional tool handle.

A second form of the present invention is a robotic actuation system employing a robotic workstation and the aforementioned robotic actuator for controlling one or actuation dials of a interventional tool handle. In operation, the robotic workstation generates motor commands for controlling the actuation dial(s) of the interventional tool handle, and the robotic actuator controls the actuation dial(s) of the interventional tool handle responsive to the motor commands generated by the robotic workstation. To this end, the motorized gear(s) are operably connected to the robotic workstation to control the actuation dial(s) of the interventional tool handle.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

FIG. 5 illustrates an exemplary embodiment of a robotic actuator in accordance with the present invention.

FIGS. 6A and 6B respectively illustrate exemplary embodiments of a probe handle base and a probe handle cover in accordance with the present invention.

Figure 7:
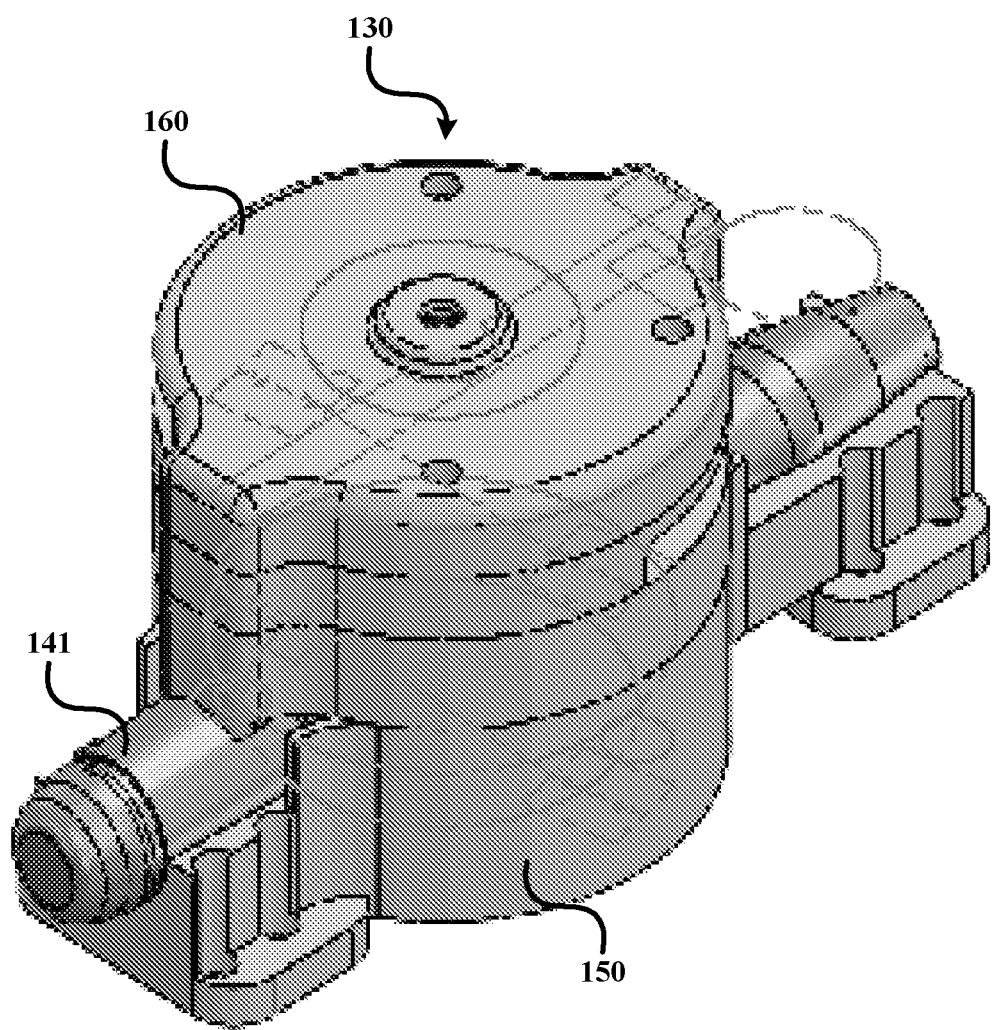

FIG. 7 illustrates a schematic embodiment of the probe handle base and the probe handle cover shown in FIGS. 6A and 6B in accordance with the present invention.

Figure 8A:
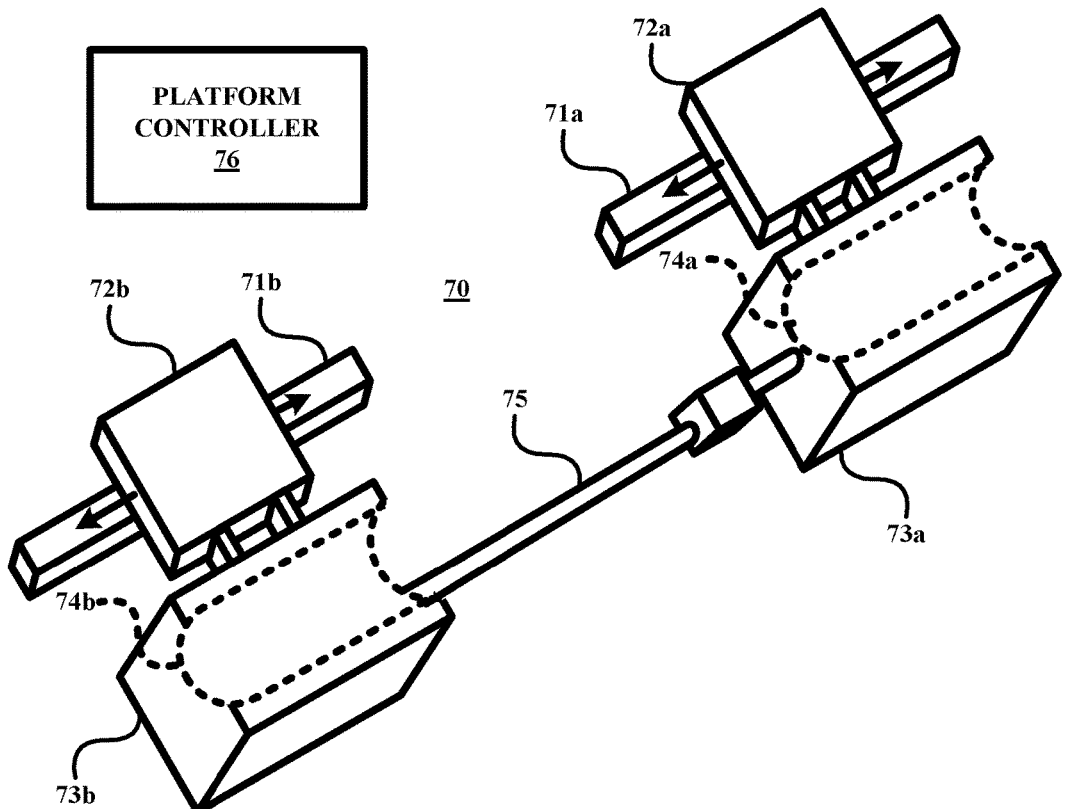
Figure 8B:
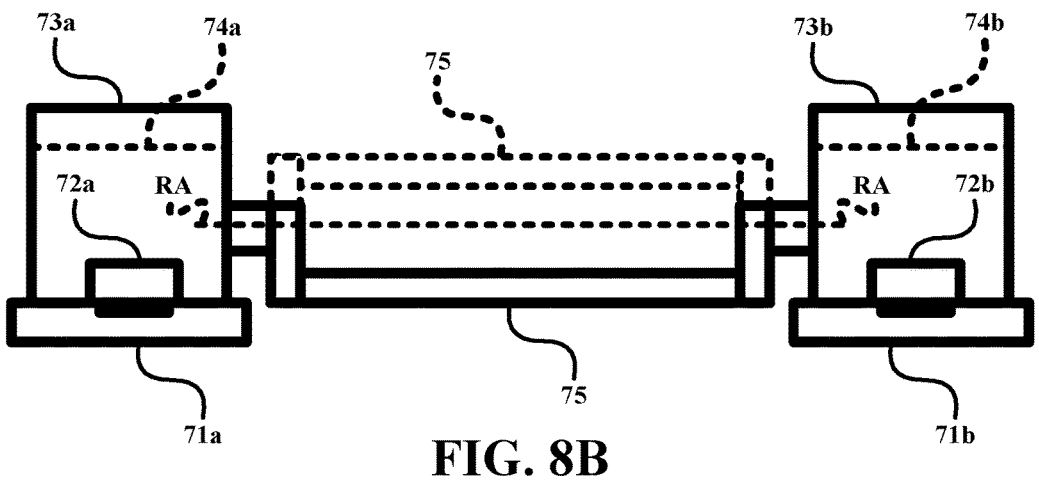

FIGS. 8A and 8B illustrate an exemplary embodiment of an actuator platform in accordance with the present invention.

FIGS. 9A-9D illustrate an operation of the actuator platform shown in FIGS. 8A and 8B.

Figure 3:
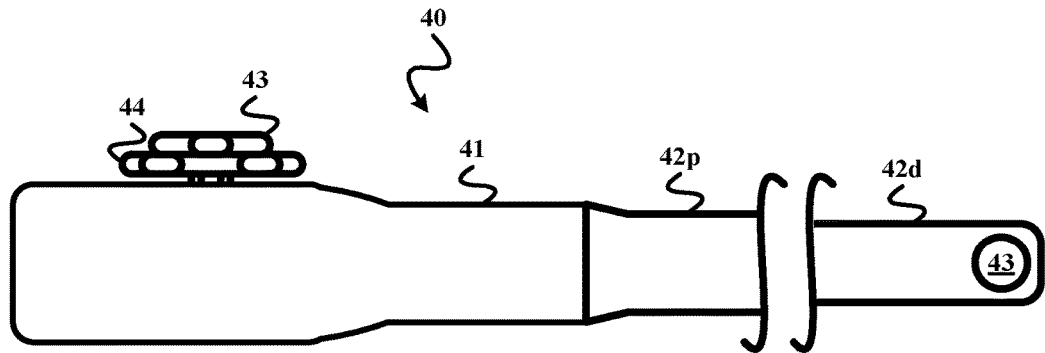
FIG. 3 illustrates an exemplary TEE probe as known in the art.

To facilitate an understanding of the present invention, exemplary embodiments of a robotic actuation system of the present invention and various components therefore will now be described in the context of a remote control actuation of a TEE probe as shown in FIG. 3. From these descriptions, those having ordinary skill in the art will appreciate how to apply the principles of a robotic actuation system of the present invention to any suitable designs of ultrasound probes for any type of procedure as well as other tendon driven flexible devices (e.g., colonoscope, gastroscope, etc.).

Referring to FIG. 3, a TEE probe 40 as known in the art employs a handle 41 and an elongated probe having a proximal end 42*p* attached to handle 41 and a distal head end 42*d* with an ultrasound transducer 43. TEE probe 40 employs a yaw actuation dial 43 for adjusting a yaw degree freedom of probe head 42*d*, and a pitch actuation dial 44 for adjusting a pitch degree freedom of probe head 42.

Figure 4A:
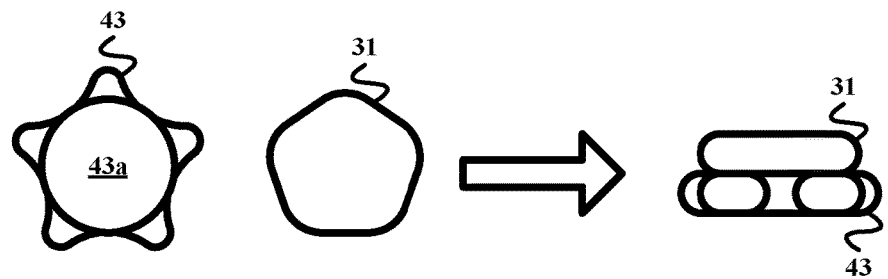
FIGS. 4A and 4B illustrate an exemplary engagements of an actuation dial of the TEE probe shown in FIG. 3 and a motorized gear in accordance with the present invention.
Figure 4B:
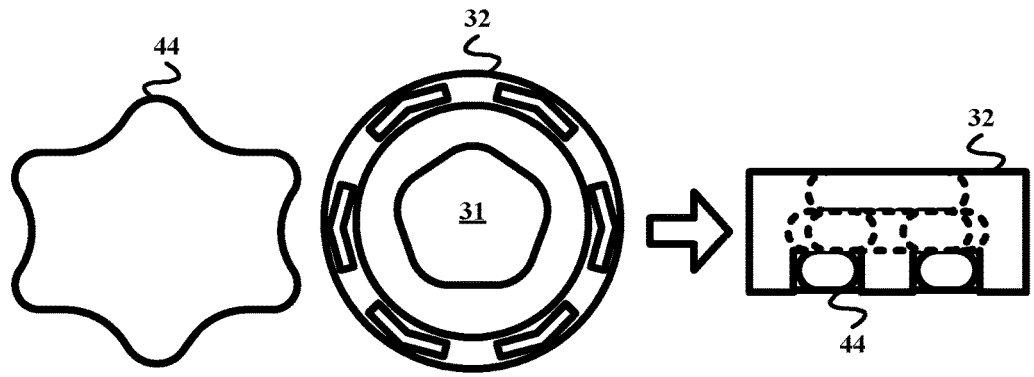

The present invention provides gears that are motorized to control an actuation of yaw actuation dial 43 and pitch actuation dial 44. For example, as shown in FIG. 4A, a friction gear 31 of the present invention is designed to frictionally engage with yaw actuation dial 43 to transmit sufficient torque for controlling a rotation of yaw actuation dial 43. By further example, as shown in FIG. 4B, a crowned gear 32 of the present invention is designed to mechanically engage with pitch actuation dial 44, without contacting yaw actuation dial 43, for controlling a rotation of pitch actuation dial 44.

Figure 2:
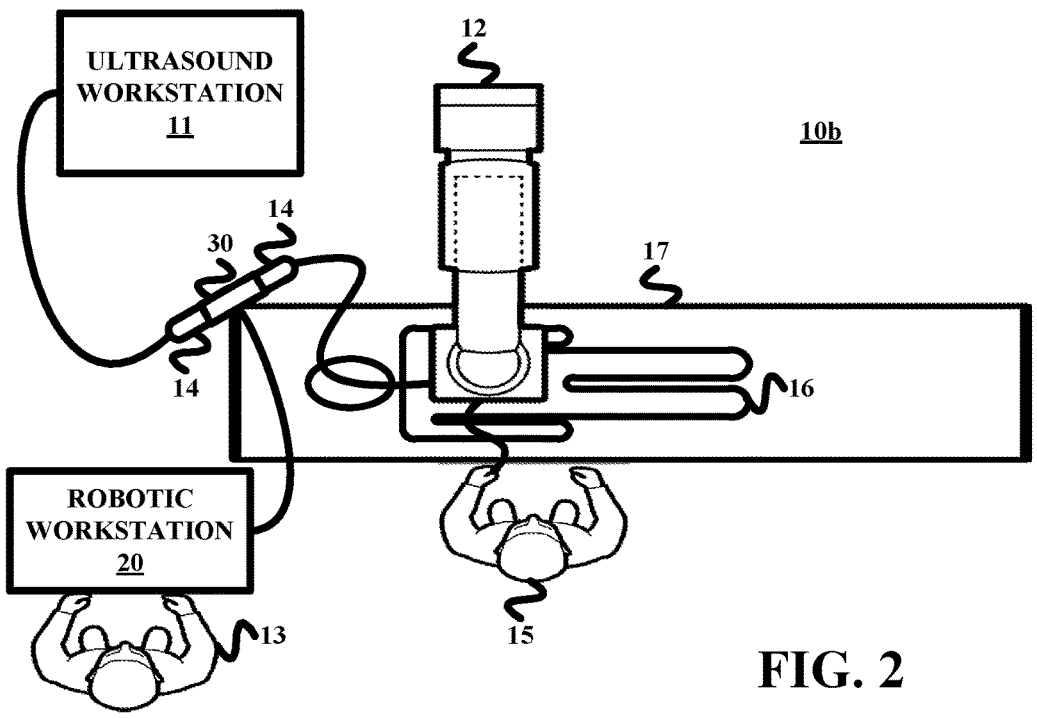
FIG. 2 illustrates an exemplary embodiment of a remote controlled actuation of a TEE probe in accordance with the present invention.

While in practice a design of a gear of robotic actuator 30 (FIG. 2) will be dependent upon a design of a corresponding actuation dial of a probe intended to be engaged thereby, embodiments of robotic actuator 30 will be described herein in the context of gears 31 and 32.

Referring to FIG. 5, one embodiment of robotic actuator 30 employs a probe handle cover 33 having a concave inner surface 33*a* and a probe handle base 34 having a concave inner surface 33*b* for defining a actuation chamber upon being magnetically coupled via one or more magnetic couplers 37. In operation, the chamber houses the actuation dials of the probe and the magnetic coupling provides an advantage of facilitating an easy removal of the probe is desired, particularly if operating circumstance dictate manual control of the probe.

Robotic actuator 30 further employs a motor 35 and a motor controller 36 ("MCONTROLLER") for each gear 31 and 32 yielding motorized gears controllable by robotic workstation 20 (FIG. 2) via an electrical coupling of robotic workstation 20 to motor controller 36. In operation, the motorized gears are sufficient to engage and rotate the actuation dials of the probe, which facilitates a lightweight design of probe handle cover 33.

Additionally, depending upon the environment within robotic actuator 30 is being operated (e.g., an operating room), probe handle base 34 and/or an actuator platform 38 as known in the art may be utilized to secure robotic actuator 30 to a frame of reference within the environment. For example, probe handle base 34 and/or actuator platform 38 may be mounted to a fixture, an operating table, operating equipment or otherwise any object for securing robotic actuator 30 to the frame of reference within the operating room.

Referring to FIGS. 6A and 6B, a schematic embodiment of robotic actuator 30 employs a probe handle base 50 and a probe handle cover 60 for controlling the actuation dials of a probe (e.g., probe handle 41 as shown). Specifically, probe handle cover 50 has a concave inner surface 51 and probe handle base 60 has a concave inner surface 61 for defining a actuation chamber upon being magnetically coupled via magnetic 52*a* of probe handle base 50 and steel locator pins 62*b* of probe handle cover 60.

Probe handle base 50 employs motor control boards 53 electrically connected to robotic workstation 20 (FIG. 2), and probe handle cover 60 employs motor control boards 63 electrically connected to motors 64 (e.g., brushed DC motors via two (2) spur gears). Motor control boards 53 and 63 having electrical contacts (not shown)(e.g., spring contacts) that are engaged upon a magnetic coupling of probe handle base 50 and probe handle cover 60 to form motor controllers. Motor controller 53*a*/63*a* implements a current control of motor 64*a* to a crowned gear 65 to thereby control a rotation of crowned gear 65. Similarly, motor controller 53*b*/63*b* implements a current control of motor 64*b* to a friction gear 66 concentric with crowned gear 65 to thereby control a rotation of friction gear 66.

FIG. 7 illustrates an aesthetic practical view of a robotic actuator 130 having a magnetic coupling of a probe handle base 150 and a probe handle cover 160 for housing and controlling actuation dials (not shown) of a probe handle 141.

FIGS. 8A and 8B illustrate one embodiment 70 of actuator platform 38 (FIG. 5) employing a pair of rails 71, a pair of sliders 72, a pair of rotation motors 73, and a crank shaft 75. By techniques known in the art, sliders 72 are slidably coupled to rails 71 and affixed to rotation motors 73, and crank shaft 75 is rotatably coupled to rotation motors 73. In operation, a platform controller 76 employs hardware, software, firmware and/or circuitry for laterally moving of crank shaft 75 via conventional control of a sliding of sliders 72 along rails 71 in one of the arrow directions and for revolving crank shaft 75 about a rotational axis RA via a control of rotation motors 73 (e.g., 180° revolution as shown in FIG. 8B). In practice, rotation motors 73 may have groves 74 for supporting a portion of the probe handle, the probe itself, and/or cabling of the probe.

Figure 9A:
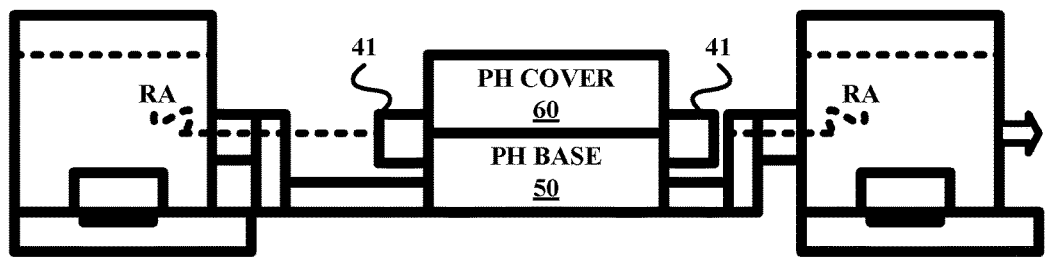
Figure 9B:
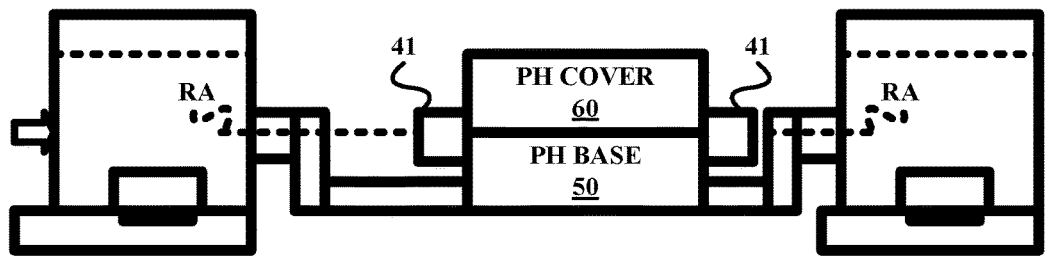
Figure 9C:
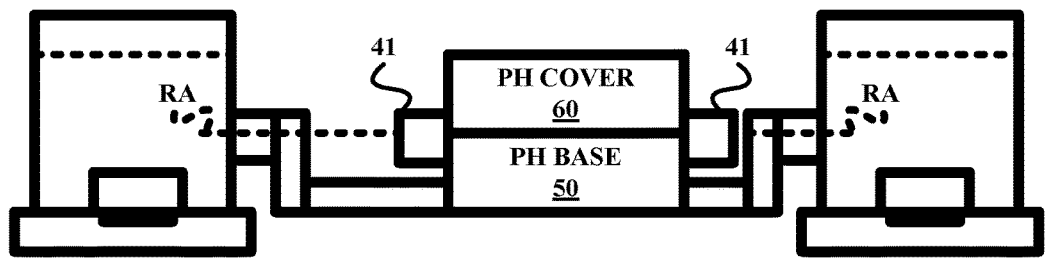
Figure 9D:
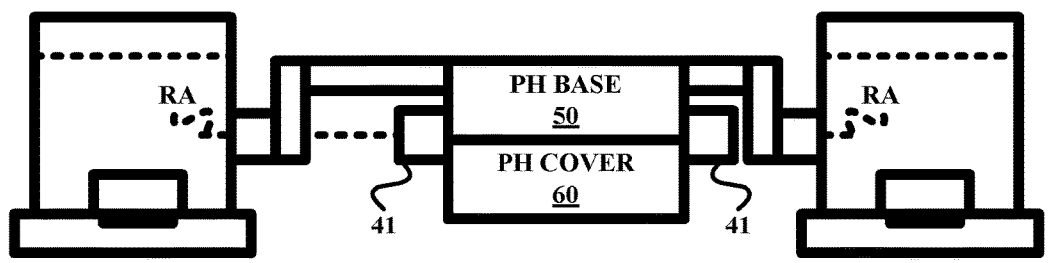

The importance of crank shaft 75 is to maintain a rotational alignment of the probe handle with rotation axis RA as crank shaft 75 is laterally moved as exemplary shown by the arrows in FIGS. 9A and 9B, or is revolved around rotational axis RA as shown in FIGS. 9C and 9D. Specifically, crank shaft 75 extends through probe handle ("PH") base 50 and probe handle 41 as seated between probe handle base 50 and probe handle cover 60 is rotationally aligned with rotational axis RA. As such, lateral movement of crank shaft 75 via control of laterally sliding sliders 72 on rails 71 will laterally move probe handle 40 in rotationally alignment with rotational axis RA as exemplary shown in FIGS. 9A and 9B. Furthermore, revolving motion of crank shaft around rotational axis RA via control of rotation motors 73 will rotate probe handle 40 about rotational axis RA as exemplary shown in FIGS. 9C and 9D.

In practice, actuator platform 70 as shown in FIG. 7 provides an additional two (2) degrees for freedom of lateral motion and rotational motion for a distal head 42*d* of probe 40 capable of being pitched and/or yawed.

Figure 1:
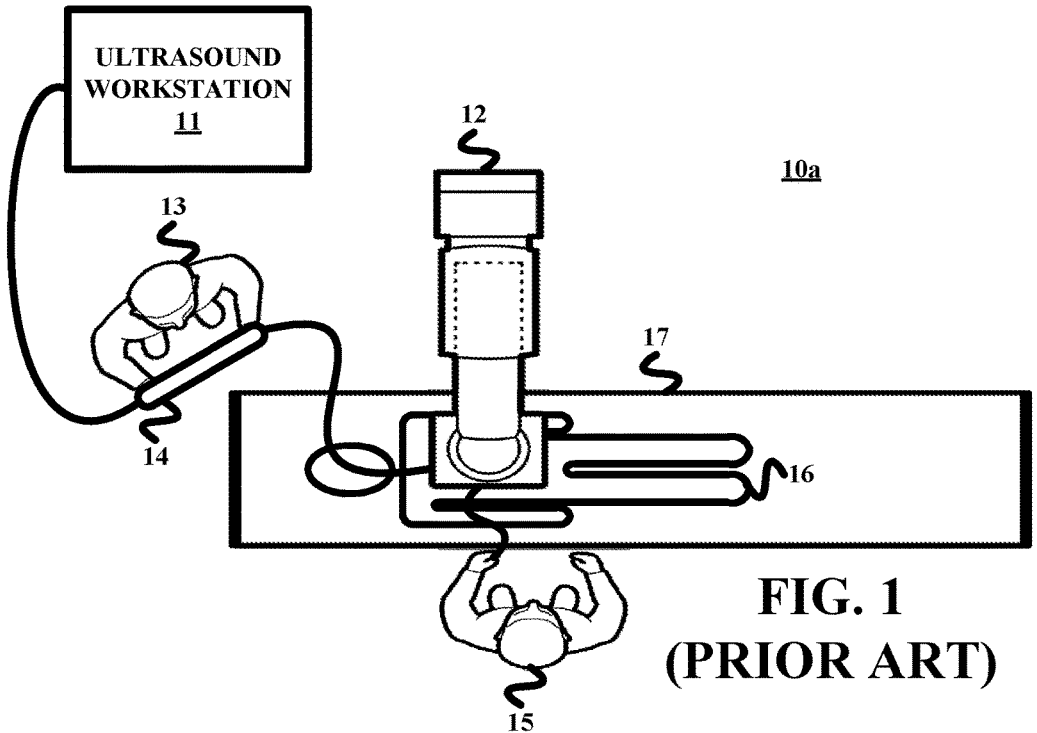
FIG. 1 illustrates an exemplary manual actuation of a TEE probe as known in the art.

Referring back to FIG. 1, robotic workstation 20 is structurally configured with hardware, software, firmware and/or circuitry as known in the art for executing technique(s) to generate motor commands to the motorized gear of robotic actuator 30 via user input. In practice, robotic workstation 20 may implement any known technique(s) for generating motor commands for a particular actuation scheme of a subject probe. More particularly to TEE probe 14, robotic workstation 20 executes known technique(s) for generating the motor commands to control a pitch degree of freedom and a yaw degree of freedom of a distal head of probe 14. Additionally, if actuator platform 70 or any other actuator platform facilitating lateral motion and rotational motion of the distal head of probe 14, the controller of the actuator platform may be a stand-alone controller, coupled to robotic workstation 20 or incorporated within robotic workstation 20. When the controller of the actuator platform is coupled to or incorporated within robotic workstation 20, robotic workstation 20 is structurally configured with hardware, software, firmware and/or circuitry as known in the art for executing known technique(s) to generate motion commands to the controller of the actuator platform via user input.

Also in practice, robotic workstation 20 may implement known component(s) and scheme(s) for interfacing with one or more users of the robotic actuation system. More particularly to FIG. 1, in a direct control scheme, robotic workstation 20 employs appropriate user interfaces (not shown) (e.g., joystick, mouse, touch-screen, etc.) for facilitating direct control of the head of TEE probe 14 by echocardiographer 13. In a collaborative control scheme, robotic workstation 20 employs appropriate user interfaces (not shown) (e.g., joystick, mouse, touch-screen, etc.) for facilitating shared control of the head of TEE probe 14 by echocardiographer 13 and cardiologist 15.

Referring to FIGS. 1-9, those having ordinary skill in the art will appreciate numerous benefits of the present invention including, but not limited to, (1) a remote control of one or more degrees of freedom of an ultrasound probe by a robotic workstation of the present invention, which adjust the ultrasound imaging volume of the ultrasound probe, (2) an ability to retrofit a robotic actuator of the present invention to existing ultrasound probes, and (3) an ability to rapidly remove a robotic actuator of the present invention from the ultrasound probe should an echocardiographer or other staffer decide to return to manual operation for any reason.

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A robotic actuator for controlling a plurality of actuation dials of an interventional tool handle, the robotic actuator comprising:
   a handle base and a handle cover coupled together to define an actuation chamber for housing the plurality of actuation dials of the interventional tool handle; and
   a plurality of motorized gears operable to engage the plurality of actuation dials, respectively, of the interventional tool handle within the actuation chamber,
      wherein a shape of at least one of the motorized gears is non-complementary to the shape of at least one of the actuation dials.

2. The robotic actuator of claim 1,
   wherein the handle base is designed to longitudinally seat the interventional tool handle; and
   wherein the handle cover is designed to cover a longitudinal seating of the interventional tool handle by the handle base.

3. The robotic actuator of claim 1, wherein the plurality of motorized gears includes:
   a first motorized gear operable to frictionally engage a first actuation dial of the interventional tool handle.

4. The robotic actuator of claim 3, wherein the plurality of motorized gears includes:
   a second motorized gear operable to mechanically engage a second actuation dial of the interventional tool handle independently of the first actuation dial.

5. The robotic actuator of claim 1, wherein the handle base and the handle cover are operable to magnetically coupled to define the actuation chamber.

6. The robotic actuator of claim 1, further comprising:
   at least one motor controller including components distributed between the handle base and the handle cover, wherein the coupling of the handle base and the handle cover connects the components of the at least one motor controller.

7. The robotic actuator of claim 1, further comprising:
   an actuator platform operably connected to the handle base to facilitate at least one of lateral motion and rotational motion of the interventional tool handle.

8. A robotic actuation system for controlling plurality of actuation dials of an interventional tool handle, the robotic actuation system comprising:
   a robotic workstation operable to generate motor commands for controlling the plurality of actuation dials of the interventional tool handle; and
   a robotic actuator operable to control the plurality of actuation dials of the interventional tool handle, wherein the robotic actuator includes:
      a handle base coupled to a handle cover to define an actuation chamber for housing the plurality of actuation dials of the interventional tool handle,
      plurality of motorized gears operable to engage the plurality of actuation dials of the interventional tool handle within the actuation chamber, a shape of at least one of the motorized gears being non-complementary to the shape of the at least one of the actuation dials, and
      an operable connection of the plurality of motorized gears to the robotic workstation to control the plurality of actuation dials of the interventional tool handle responsive to the motor commands generated by the robotic workstation.

9. The robotic actuation system of claim 8,
   wherein the handle base is designed to longitudinally seat the interventional tool handle; and
   wherein the handle cover is designed to cover a longitudinal seating of the interventional tool handle by the handle base.

10. The robotic actuation system of claim 8, wherein the plurality of motorized gears includes:
    a first motorized gear) operable to frictionally engage a first actuation dial of the interventional tool handle.

11. The robotic actuation system claim 10, wherein the plurality of motorized gears includes:
    a second motorized gear (operable to mechanically engage a second actuation dial of the interventional tool handle.

12. The robotic actuation system of claim 8, wherein the handle base and the handle cover are operable to magnetically coupled to define the actuation chamber.

13. The robotic actuation system of claim 8, further comprising:
- at least one motor controller including components distributed between the handle base and the handle cover,
    - wherein the coupling of the handle base and the handle cover connects the components of the at least one motor controller.

14. The robotic actuation system of claim 8, further comprising:
- an actuator platform operably connected to the handle base to control at least one of lateral motion and rotational motion of the interventional tool handle.

15. The robotic actuation system of claim 14,
- wherein the robotic actuation workstation is operable to generate motion commands for controlling at least one of lateral motion and rotational motion of the interventional tool handle; and
- wherein the actuator platform is operably connected to control at least one of lateral motion and rotational motion of the interventional tool handle responsive to the motion commands.

* * * * *